United States Patent [19]
Martin et al.

[11] 4,204,524
[45] May 27, 1980

[54] METHOD AND APPARATUS FOR CONTROLLING CARDIAC ASSIST DEVICE

[76] Inventors: Peter J. Martin, 52A Pomfret Rd., Narragansett, R.I. 02882; Dov Jaron, 66 White Horn Dr., Kingston, R.I. 02881

[21] Appl. No.: 849,133
[22] Filed: Nov. 7, 1977
[51] Int. Cl.² .............................................. A61H 31/00
[52] U.S. Cl. ..................................................... 128/1 D
[58] Field of Search ............. 128/1 D, 2.05 R, 2.06 R

[56] References Cited
U.S. PATENT DOCUMENTS

| | | | |
|---|---|---|---|
| 3,750,644 | 8/1973 | Ragsdale | 128/1 D |
| 3,783,453 | 1/1974 | Bolie | 128/1 D |
| 3,835,845 | 9/1974 | Maher | 128/2.06 R |
| 3,871,360 | 3/1975 | Van Horn et al. | 128/2.06 R |
| 3,985,123 | 10/1976 | Herzlinger et al. | 128/1 D |
| 4,016,871 | 4/1977 | Schiff | 128/1 D |
| 4,023,563 | 5/1977 | Reynolds | 128/2.06 R |
| 4,051,841 | 10/1977 | Thoma | 128/2.05 R |

Primary Examiner—William E. Kamm
Attorney, Agent, or Firm—Thompson, Birch, Gauthier & Samuels

[57] ABSTRACT

Method and apparatus for controlling in-series cardiac assist devices which uses the afterload phase angle as the operating criterion. The phase of the pump driving waveform is controlled with a single adjustment. The time interval from the R-wave to midpump systole is used and the phase angle of the pump driving waveform is determined only by this control parameter. The duration of pump systole is thus symmetric about the TMPS adjustment and can be changed without disturbing this phase angle.

13 Claims, 12 Drawing Figures

| TIME (msec) | CONTROL COUNTER | CLOCK RATE | START COUNTER | STOP COUNTER | WORK COUNTER |
|---|---|---|---|---|---|
| 0 | 0 | 0 | 0 | 0 | 0 |
| 100 | 100 | 0 | 0 | 0 | 0 |
| 100+ | 100 | 1 MHz | TMPS | TMPS | 1/2 DUR |
| 100-101 | 100 | 1 MHz | $T_{act}$ | $T_{deact}$ | 0 |
| 101- | 100 | 1 KHz | $T_{act}$ | $T_{deact}$ | TMPS |
| 101 | 101 | 1 KHz | $T_{act}$ | $T_{deact}$ | TMPS-1 |
| $T_{act}$ | $T_{act}$ | 1 KHz | 100 | | |
| TMPS | TMPS | 1 KHz | | | 100 |
| $T_{deact}$ | $T_{deact}$ | 1 KHz | | 100 | |

METHOD AND APPARATUS FOR CONTROLLING CARDIAC ASSIST DEVICE

BACKGROUND OF THE INVENTION

This invention relates to an apparatus for assisting the natural action of a defective heart and more particularly to a heart pump, such as an intra-aortic balloon which is synchronized with the patient's heart.

An intra-aortic balloon is a device which is designed to augment diastolic pressure and flow in a manner which displaces a given volume of blood from the thoracic aorta in diastole. In addition the rapid collapse of the intra-aortic balloon prior to the onset of systole produces a reduction in systolic pressure and if properly timed, has a vacuum-like effect, assisting in the ejection of left ventricular contents during early systole. In this manner, there is a sharp reduction in the left ventricular systolic afterload, improving left ventricular emptying and thus reducing left ventricular end-diastolic volume over a period of time. With reduction in left ventricular end-diastolic volume and therefore, end-diastolic pressure, and a diastolic augmentation of coronary artery pressure, the subendocardial coronary circulation may be markedly improved.

To achieve these goals the balloon should ideally possess the properties of rapid inflation and deflation. This provides a source of momentum in diastole propelling the blood forcefully into the systemic circulation, and a source of vacuum momentum during deflation to augment the ejection of blood from the left ventricle in systole.

Another property vital to efficient balloon performance is timing of inflation and deflation to correspond exactly with the events of systole and diastole as initiated by the patient's cardiac rhythm. Early inflation of the balloon occuring during the latter part of the ventricular systole, will reduce left ventricular emptying. In a similar manner late deflation of the balloon (that is, during the initial phase of the ventricular systole) will augment rather than reduce ventricular afterload. Late inflation of the balloon after the onset of diastole; may not achieve the same degree of diastolic augmentation. Early deflation of the balloon prior to the onset of systole will produce a premature intra-aortic vacuum which may induce a reversal of coronary flow by allowing the reaccumulation of systemic blood in the aorta will thwart the effectiveness of the systolic afterload reduction.

At present, the methods of controlling in-series cardiac assist devices, particularly of the intra-aortic type, are subjective in nature and adjustments are performed manually by trained operators. Only recently have research efforts been directed toward finding objective criteria for controlling these devices. Clark et al, the "Feasibility of Closed Loop Control of Intra-Aortic Balloon Pumping", IEEE Trans. Bme 20, 404–412 (1973) and Williams et al, the "Control Criteria for Intra-Aortic Balloon Pumping", Proc. 28 Acemb, 349 (1975).

Timing is a critical property in the use of intra-aortic devices. Present commercial devices typically employ two timing adjustments to control the assist device. The first is the time interval from the ECG R-wave to pump activation (termed "delay") and the second is the time interval from activation to deactivation of the device (termed "duration" of the pump systole). A change in either of these adjustments will alter the phase of the driving waveform and hence the afterload phase angle. Patents of interest in this area are U.S. Pat. Nos. 3,426,743; 3,430,634; 3,452,739; and 3,966,358. In these references timing adjustments include the delay from the ECG R-wave to either pump systole or pump diastole.

To perform a well controlled study of the relationship between the afterload phase angle and hemodynamic effects of cardiac assistance a control unit is needed which allows accurate, reproducible and convenient control of the phase angle. Such control is not possible with conventional units. Thus there exists a need for a device capable of controlling the afterload phase angle.

BRIEF SUMMARY OF THE INVENTION

The present invention comprises a method and apparatus which activates and deactivates an in-series cardiac assist device during the cardiac cycle. Generally the conventional "delay" from the ECG R-wave to device activation is replaced by the time interval from the R-wave to mid-pump systole (TMPS). The "duration" of the pump systole is symmetrical about the TMPS and does not affect the phase difference between the heart and pump cycles.

The apparatus of the invention, and more particularly a control module generates a driving waveform which activates the assist device at the proper time during the cardiac cycle. This driving waveform is synchronized to the cardiac cycle using the R-wave of the electrocardiogram.

In the preferred embodiment of the invention the phase angle of the device driving waveform is controlled with a single adjustment namely the time interval from the R-wave to mid pump systole defined as TMPS (mid-left ventricular diastole). The phase angle of the device driving waveform is determined only by the TMPS. The duration of activation is now symmetric about the TMPS adjustment and can be changed without disturbing the phase angle.

The invention broadly comprises a control module which receives ECG signals and activates and deactivates an assist device such as an intra-aortic balloon.

The control module includes a data selection unit, a timing unit with an associated timing control and a control logic. The control module may be operated manually or automatically.

When the assist device is to be activated, the output of the control logic goes to high. When the assist device is to be deactivated, the output returns to low. The control logic is triggered by the ECG R-wave and produces a pulse waveform which is in synchrony and out of phase with the cardiac cycle. The time of activation and the time of deactivation are generated from two timing adjustments. The first TMPS is timed from the ECG R-wave to midpump systole. The second one-half DUR is one-half the duration of the pump systole.

In the preferred embodiment, the phase angle of the pump driving waveform can be controlled to an accuracy of 1° and timing adjustments accurate to 1 msec satisfy this criteria for heart rates of up to 166 beats per minute. Provision is made to insure that premature ventricular beats (PVC) will deactivate the assist device if such a PVC occurs while the assist device is active.

Broadly, in our invention, the afterload phase angle is used as an operating criterion for an in-series assist device. The assist device which generates the pressure pulse in the aorta during diastole is controlled by a driving waveform from the control module. Conventional units set delay from the ECG R-wave to pump activation and the duration causes a change in the phase of the pump driving waveform which results in a change in the afterload phase angle. Our control module allows the phase of the pump driving waveform to be controlled with a single adjustment, namely the TMPS. The phase angle of the driving waveform is determined only by this new control parameter. The duration is symmetric about the TMPS adjustment and can be changed without disturbing this phase angle.

BRIEF DESCRIPTION OF THE DRAWINGS

FIG. 6 is a diagram of the control logic;

DESCRIPTION OF THE PREFERRED EMBODIMENT

Figure 1:
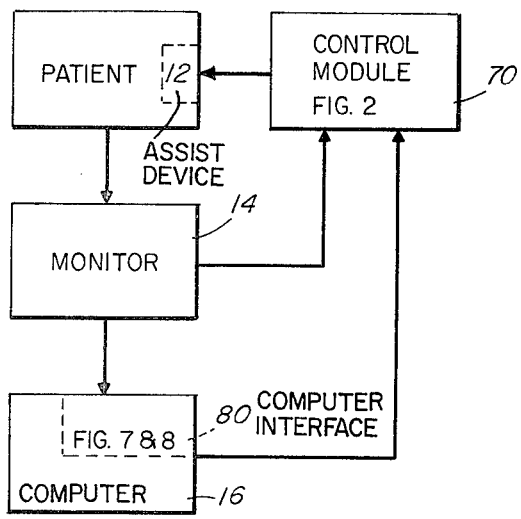
FIG. 1 is a block diagram of an embodiment of the invention in a total system concept.

The invention will be described in reference to an intra-aortic assist device. Referring to FIG. 1, a control module 10 controls the activation and deactivation of an assist device such as an intra-aortic balloon identified as 12. The ECG information from the patient is transmitted to a monitor 14. The ECG information from the monitor 14 will be transmitted directly to the control module 10 when in manual mode or alternatively when in automatic mode will be transferred both to an interface 80 of a computer 16 and to the control module 10.

The intra-aortic device, its inflation and deflation in response to signals and the receipt and transmission of ECG signals from a patient to a control unit are well known in the art and need not be described in detail.

Figure 2:
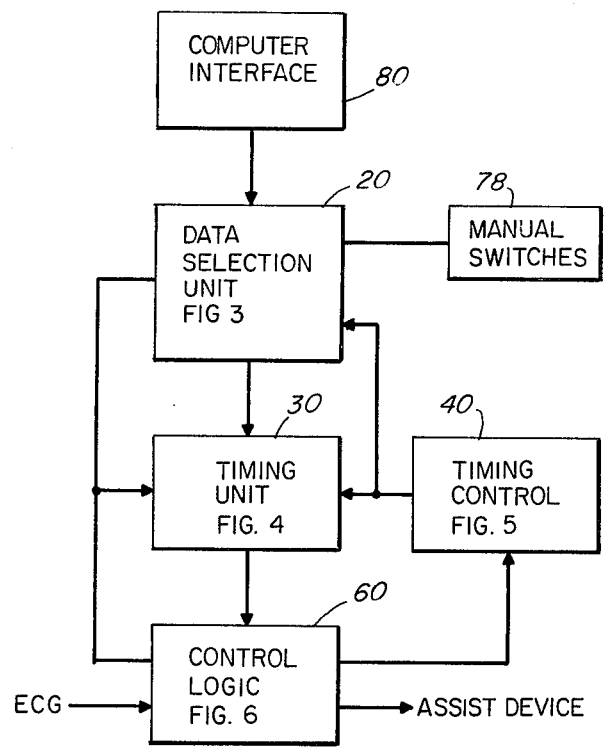
FIG. 2 is a functional block diagram of the control module of the invention.

Referring to FIG. 2, the control module 10 is shown as a functional block diagram and comprises a data selection unit 20, a timing unit 30, a timing control 40, and a control logic 60. In the automatic mode a computer interface 80 is used. In the manual mode switches 78, which comprise three digit BCD lever wheel switches, are used.

Data Selection Unit

Figure 3:
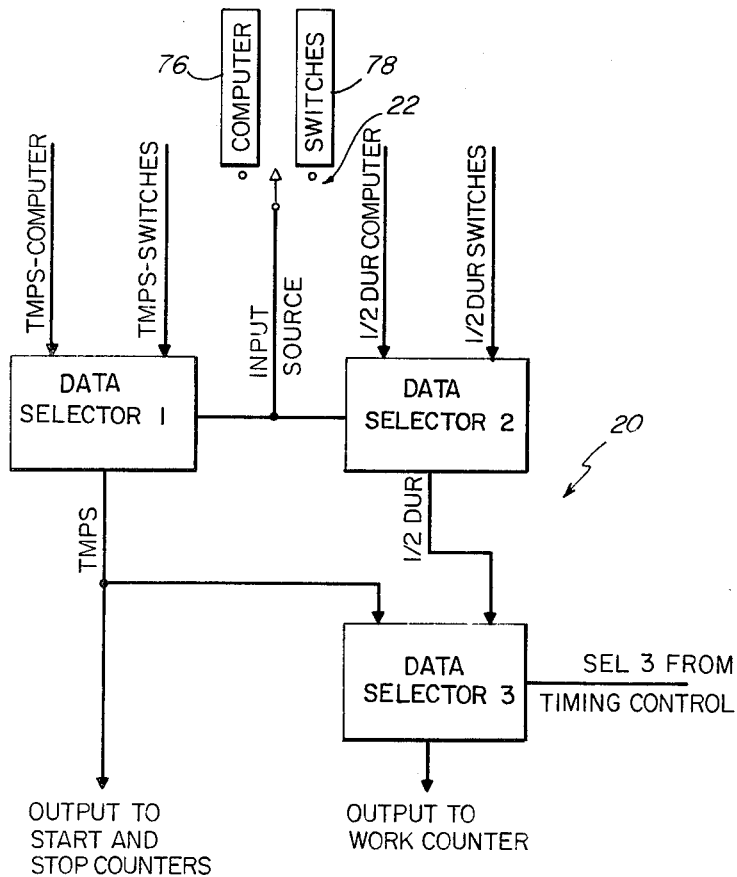
FIG. 3 is a functional block diagram of the data selector unit in the control module.

Referring to FIG. 3, the data selection unit 20 comprises three data selectors, DS1-3. The logic for the data selectors consists of three twelve bit selectors contained in five circuit boards. Each board contains two ICs. Each IC selects a four bit word from one of two sources and places that word at its outputs. Two control lines are used with each IC, one to enable or to disable the IC and the other to control which word is selected. All data selector ICs are permanently enabled.

Figure 4:
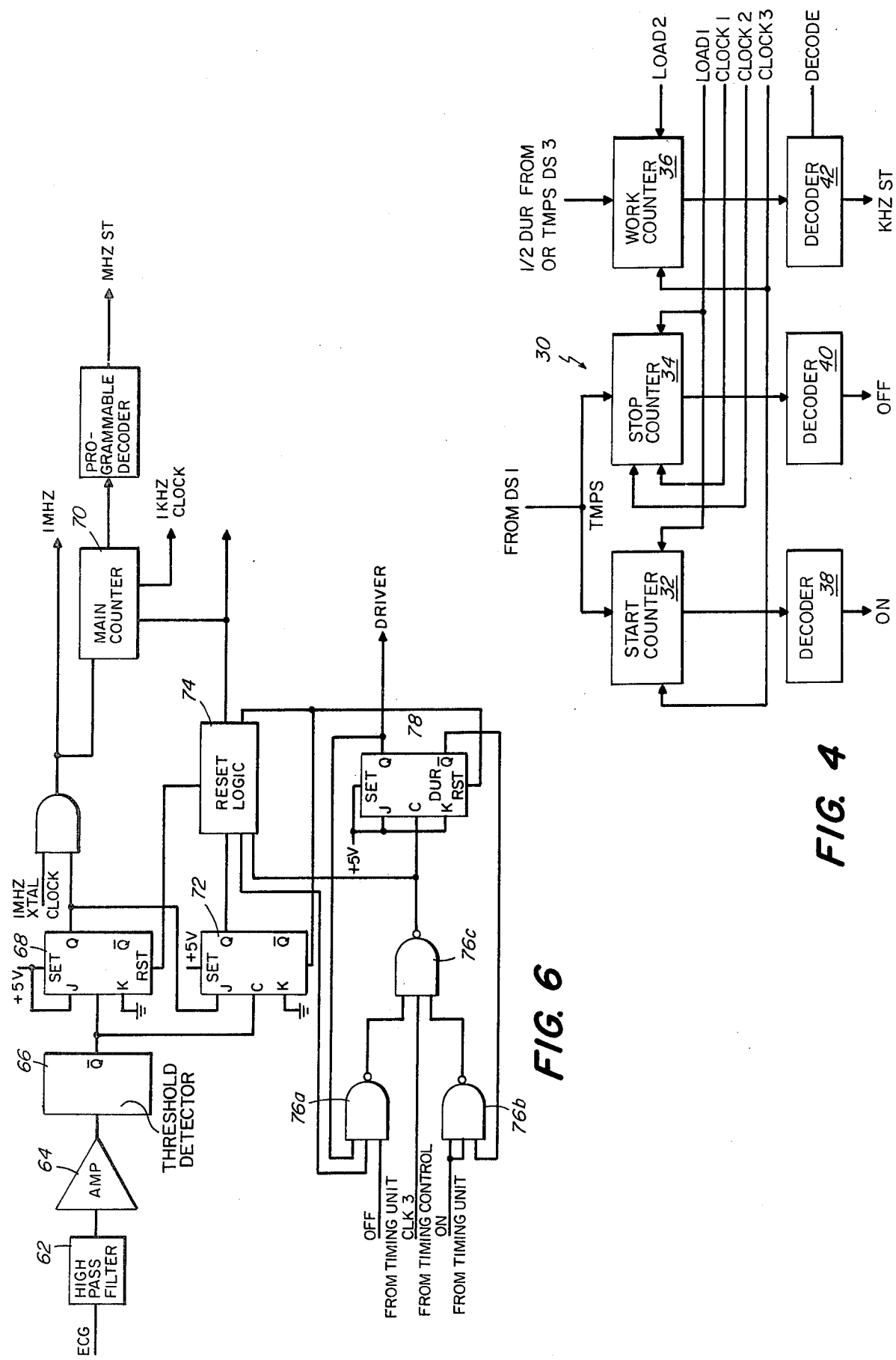
FIG. 4 is a functional block diagram of the timing unit in the control module.

Selector DS1 comprises first and third boards and selects the TMPS from either the computer 16 or the front panel switches 78. Two of the ICs on the first selector board select bits 0 through 3, and 4 through 7, respectively. Bits 8 through 11 are selected by another IC on the third selector board. The outputs of the selector DS1 are used to preset the start and stop counters 32 and 34, respectively; FIG. 4, in the timing unit 30.

Selector DS2 is contained on the second and third boards and selects one-half DUR from either the computer 16 or the front panel switches 78. The ICs on the second board select bits 0 through 3, and 4 through 7, respectively and bits 8 through 11 are selected by the third data selector board.

The outputs from the data selectors, DS1 and DS2, also go to data selector DS3 which comprises the fourth and fifth data selector boards. Bits 0 through 3 and 4 through 7 go to the fourth data selector board and bits 8 through 11 go to the fifth data selector board. On each board the enable lines from each IC are connected together and the select lines from each IC are connected together.

The select lines from DS1 and DS2 are connected together and go to the mode switch 22. The select line from selector DS3 is connected to a circuit on the timing control 40, FIG. 5, which determines which input of selector DS3 presets the work counter 36 of the timing unit 30, FIG. 4. That is, at the appropriate time either one-half DUR or the TMPS is selected to be loaded in the work counter 36 in the timing unit 30.

Timing Unit

The timing unit 30 is shown in FIG. 4. The start counter 32 of the timing unit comprises three ICs which are synchronous four bit BCD up-down counters. They are cascaded using their own internal circuitry and have a counting range from 0 to 999. Start counter 32 receives three inputs: the TMPS from data selector DS1, the countdown input from CLK3 of the timing control and a load signal both from the timing control, FIG. 5. The output from the start counter 32 goes to a decoder 38.

The stop counter 34 comprises four ICs. The counter 34 can accommodate a value of $T_{deact}$ (to be described hereinafter). Inputs to the stop counter are from the timing control, FIG. 5 and specifically LOAD 1 and CLK's 1 and 2; and from data selector DS1. The output from the counter goes to a decoder 40.

Work counter 36 comprises three ICs. This counter 36 only counts down and receives two inputs, either a one-half DUR (to be described hereinafter) or the TMPS from DS3; a LOAD 2 input and a CLK 3 input from the timing control. The LOAD 2 input is used to preset the counter 36 at two different times in the cardiac cycle. The output of the counter 36 goes to a decoder 42.

The decoders 38, 40 and 42 are fully programmable and can decode any state from 0-9999. However decoder 42 used with the work counter 36 is wired so that it can decode either the state 0 or 100. Decoders 38 and 40 are wired to decode the state 100.

Timing Control

Figure 5:
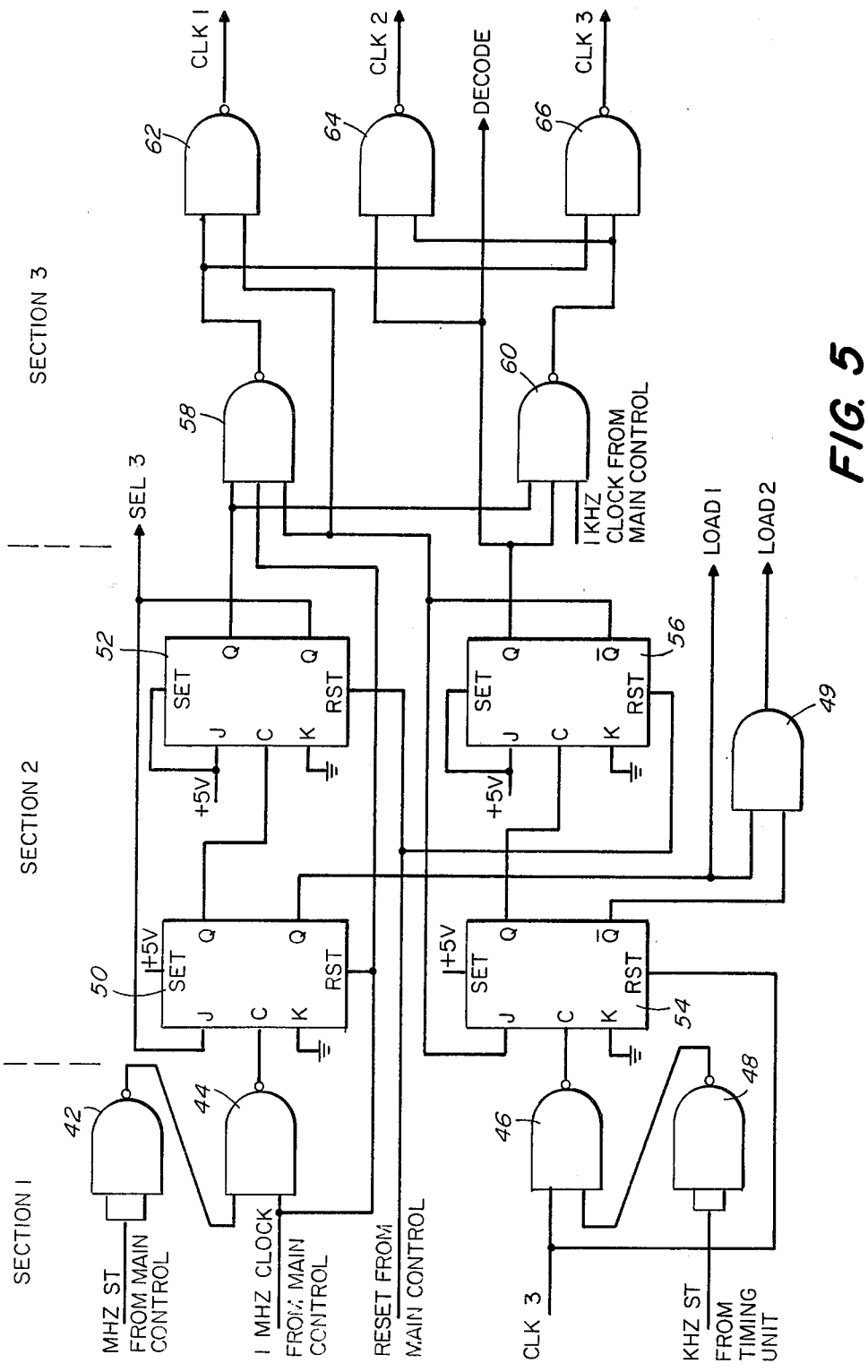
FIG. 5 is a logic diagram of the timing control.

The timing control 40 is shown schematically in FIG. 5. The purpose of the timing control logic is to insure proper operation of the timing unit 30 and data selection 20. The timing control logic is generally divided into three sections.

The first section comprises gates 42, 44, 46 and 48 and receives pulses indicating when significant events have occurred. The second section comprises a gate 49 and flip flops 50, 52, 54 and 56. This second section determines the input to data selector DS3 from flip flop 52, the state at which the work counter 36 is decoded from flip flop 56, and also generates pulses used to initialize and reset the counters 32, 34 and 36 in the timing unit 30. The third section comprises gates 58, 60, 62, 64 and 66.

In its initial state the inputs MHZ ST from control logic 60 and inputs KHZ ST from the timing unit 30 and specifically the decoder 42 are high and the flip flops 50, 52, 54 and 56 are in their off state. The outputs LOAD 1 from flip flop 50 and LOAD 2 from flip flops 50 and 54 are both high. Output SEL3 is high which will cause the work counter 36 to be preset with one-half DUR of pump systole from selector DS3 when LOAD 1 goes low. The output DECODE is low which causes decoder 42 to decode the work counter 36 at 0. A 100 msec processing period is reserved for computer processing.

When the 100 msec reserve for computer processing has been timed the control logic 60, FIG. 6, drives MHZ ST low. This triggers flip flop 50 which causes LOAD 1 to preset the counters 32, 34 and 36 with their initial values. The falling edge of 1 MHZ clock resets flip flop 50 via gate 44 which ultimately turns on clock output CLK1 by flip flop 52. This allows the 1 MHZ clock to generate the signals CLK1 and CLK3 which drives the timing unit 30.

When the work counter 36 reaches 0, KHZ ST is driven low. This turns flip flop 54 on which causes LOAD 2 to preset the work counter 36 for the second time. Because SEL3, is now low the work counter 36 will be preset with the TMPS. The falling edge of the clock pulse resets flip flop 54 which turns on flip flop 56. This turns off the 1 MHZ clock and allows the 1 KHZ clock to generate the signals CLK2 and CLK3 which drive the timing unit. When the cycle is complete RESET from the control logic is driven low and the timing control circuit is returned to its initial state.

Control Logic

The control logic 60 is shown in FIG. 6 and comprises an R-wave detector which consits of a high pass filter 62, an adjustable gain amplifier 64 and a threshold detector 66. The high pass filter 62 is used to remove baseline drift and the amplifier is used to adjust the ECG so that it is within the range of the detector. The threshold detector is simply a Schmitt Trigger input to a one shot. When the R-wave is detected a negative TTL pulse is produced and a flip flop 68 is turned on. This allows a free running 1 MHZ clock to drive a main counter 70. The counter 70 divides the 1 MHZ clock down to a 1 KHZ clock and times the 100 msec "processing" period.

A detection circuit for detecting premature ventricular beats made up of a flip flop 72 connected to reset logic 74. The flip flop 72 is set by an R-wave only if flip flop 68 has been previously set but not cleared by the normal deactivation of the assist device. This condition activates the reset logic which in turn deactivates the assist device and resets the entire control module.

The assist device control circuit consists of three NAND gates 76a, 76b, and 76c and a flip flop 78. Flip flop 78 is set when the assist device is to be activated and reset when the assist device is to be deactivated. The NAND gates insure that only the proper signals effect the assist device.

Computer Interface

Figure 7:
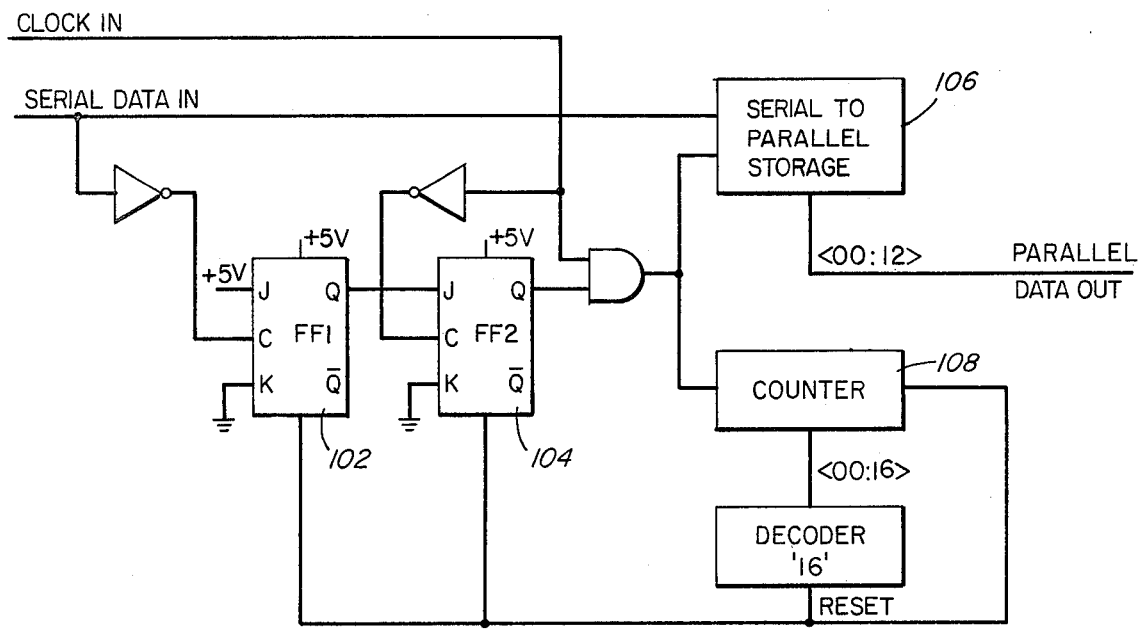
FIGS. 7 and 8 are schematics of an interface.
Figure 8:
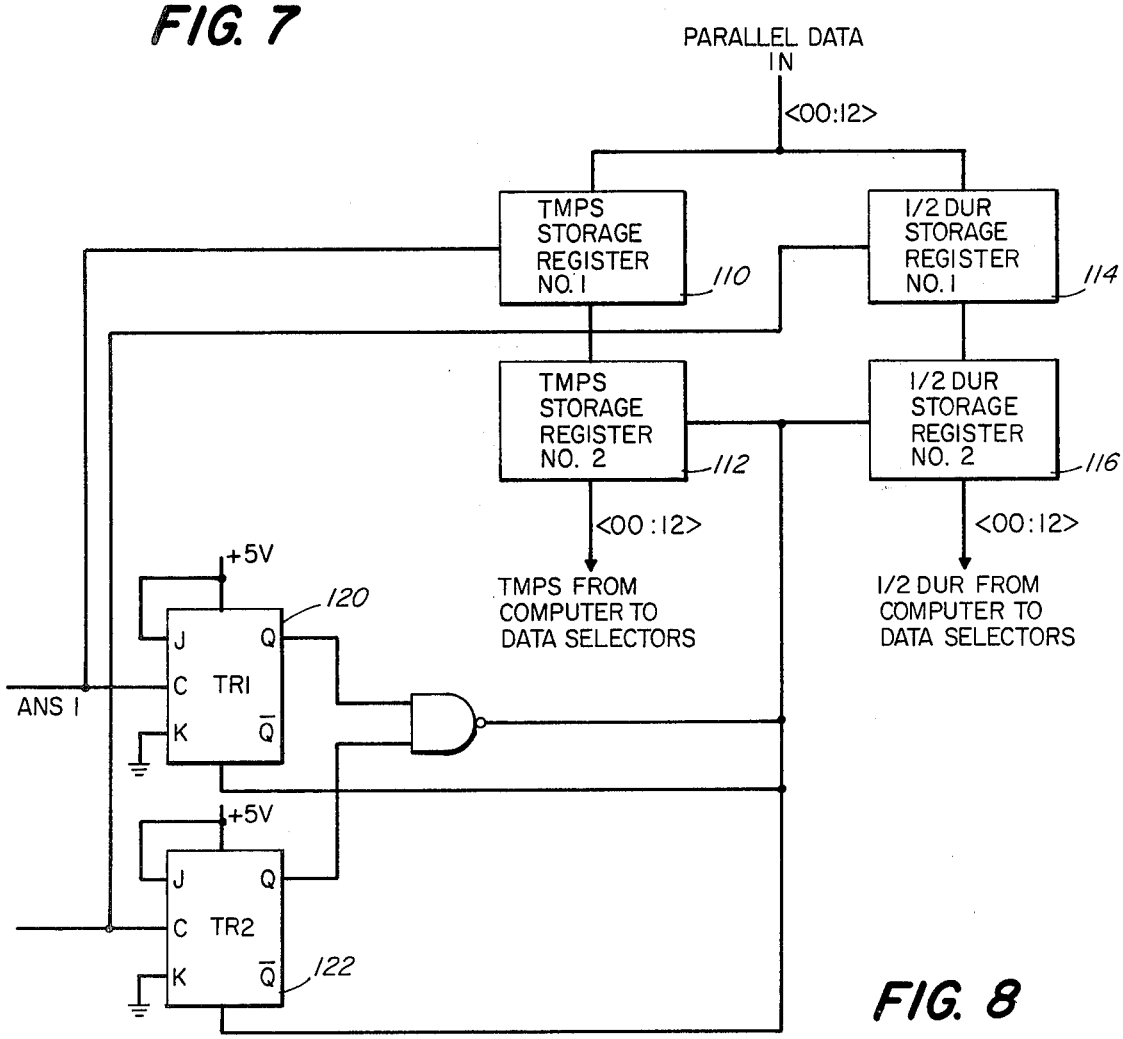

The control of the computer 10 is accomplished through the instructions. The instructions are written in terms of the particular mode of operation desired. The computer thus has stored in its memory the programs or routines corresponding to the mode of operation. As is well known to those skilled in the art the computer comprises suitable control, storage and computatable units for performing various arithmetic functions on data which is presented in digital form. Any standard computer language consistent with the capability of the computer can be used with the instructions. Also the interface used will depend on the type of digital computer. The computer is programmed to detect the R-wave and determine the TMPS and one-half DUR for each cardiac cycle. When a first R-wave is detected, the computer performs these functions. When a second R-wave is detected by both the computer and the control module the TMPS and one-half DUR derived from hemodynamic data during the first cycle are transmitted to the control module and used by the control module for control of the assist device. The computer determines the TMPS and one-half DUR from the second R-wave for use by the control module when the control module detects the third R-wave, etc. A preferred interface 80 is illustrated in FIGS. 2, 7 and 8.

Basically the computer 16 receives hemodynamic data from the monitor 14 calculates new timing adjustments, and transfers these to the control module 10. The control module receives ECG data from the monitor 14, particularly the R-wave detector of FIG. 6.

The computer 16 sends the data to the control module 10 in serial form in order to minimize the number of lines between the computer 16 and the control module 10.

Two one word transfers are required to transmit both timing adjustment values, TMPS and one-half DUR. Four lines between the computer and the control unit are used to accomplish this. One line is used to carry the serial data and a second line transmits a clock signal which is synchronous with the data signal. The third and fourth lines are used to tell the control unit which word TMPS or one-half DUR is being transmitted.

Referring to FIG. 7, the serial data consits of a start bit and 16 data bits. The computer sends the serial data and the clock signal simultaneously. The rising edge of the start bit sets flip flop 102 which then enables flip flop 104. The clock pulse associated with the first data bit sets flip flop 104. This allows the clock signals to reach the serial to parallel converter 106 and the counter 108. The converter 106 then begins receiving and shifting the data. The counter 108 is used to keep track of the number of bits which have been sent. When the counter reaches 16 a decoder 110 sends a reset pulse to both flip flops. This terminates the serial to parallel conversion. The data is now in parallel form at the outputs of the converter 106. At the end of each word transfer the data is stored in a register so that it will not be lost when another transfer is made. A double buffer storage system 110, 112, 114 and 116 is used, FIG. 8.

When the first of the two transfers is complete the computer pulses the line TRANS1 which causes the data, TMPS, at the output of the converter to be stored in the storage register 110 and frees the converter 106 for the second transfer. This also sets flip flop 120 which indicates that the first transfer is complete. At the end of the second transfer, the computer pulses line TRANS2. This stores the data one-half DUR at the outputs of the serial to parallel converter, in the register 114 and sets flip flop 122. When both flip flops have been set both words are simultaneously loaded into storage registers 112 and 116. The new timing adjustments TMPS and one-half DUR are now available for use in the control module.

Operation

In the operation of the invention the first decision is whether or not operation is going to be for manual or automatic. If operation is for manual mode then the switch 22, FIG. 3, is set to manual mode for switches 78. The switch registers, BCD lever wheel switches, are then set to provide the timing adjustments namely the TMPS and the one-half DUR. This information is derived from analysis of hemodynamic data. If the computer input is to be used then the mode switch 22 is set to computer.

In this automatic mode, the interface 80 as described above, this serial data will consist of two 12 bit words, one word for TMPS and one word for one-half DUR. These words will be read in and stored one at a time.

The ECG is used as a reference signal for the control unit and the time T=0 is defined as the occurrence of the R-wave. When the R-wave is detected the Schmitt Trigger 66 activates flip flop 68 and the counter 70 begins timing the 100 msec reserved for computer processing. As previously described, this counter 70 always counts in the positive direction at the 1 KHZ clock rate. The timing diagram of the control module is set forth in FIG. 9. The signal KHZ ST is sent to the timing control, FIG. 5, and more specifically to gate 42 and flip flop 50 when the counter 70 reaches 100.

When the timing control receives this signal it generates a load pulse LOAD 1, which presets the counters 32, 34 and 36 of the timing unit 30. In addition it enables the 1 MHZ clock to drive the three counters. The start counter 32 is preset with the value of TMPS and begins counting down. The stop counter 34 is also preset with TMPS but begins counting up. The work counter 36 is present with one-half DUR and begins counting down. When the work counter 36 reaches 0 a pulse is sent to the gate 46 of the timing control. This disables the 1 MHZ clock and resets the work counter 36 with TMPS. At this time the start counter 32 contains $T_{act}$ and the stop counter 34 contains $T_{deact}$. $T_{act}=TMPS-\frac{1}{2}DUR$ and $T_{deact}=TMPS+\frac{1}{2}DUR$. The timing control then enables the 1 KHZ clock such that all counters 32, 34 and 36 count down. This all occurs between $T=100$ and $T=101$. The first 1 KHZ clock pulse arrives at the timing unit at $T=101$. It should be noted that both the 1 MHZ and the 1 KHZ clock are in sync so that no pulses are lost when switching rates.

When the start counter reaches 100 then $T=T_{act}$. A pulse is generated, from decoder 38 to activate the assist device. This pulse would be input directly to NAND gate 76B then to flip flop 78 to drive the assist device. When the work counter reaches 100 then $T=TMPS$ and a pulse is generated for monitoring purposes only. Finally when the stop counter reaches 100 then $T=T_{deact}$ and a pulse is generated to NAND gate 76A to deactivate the assist device.

Figures 9, 10:
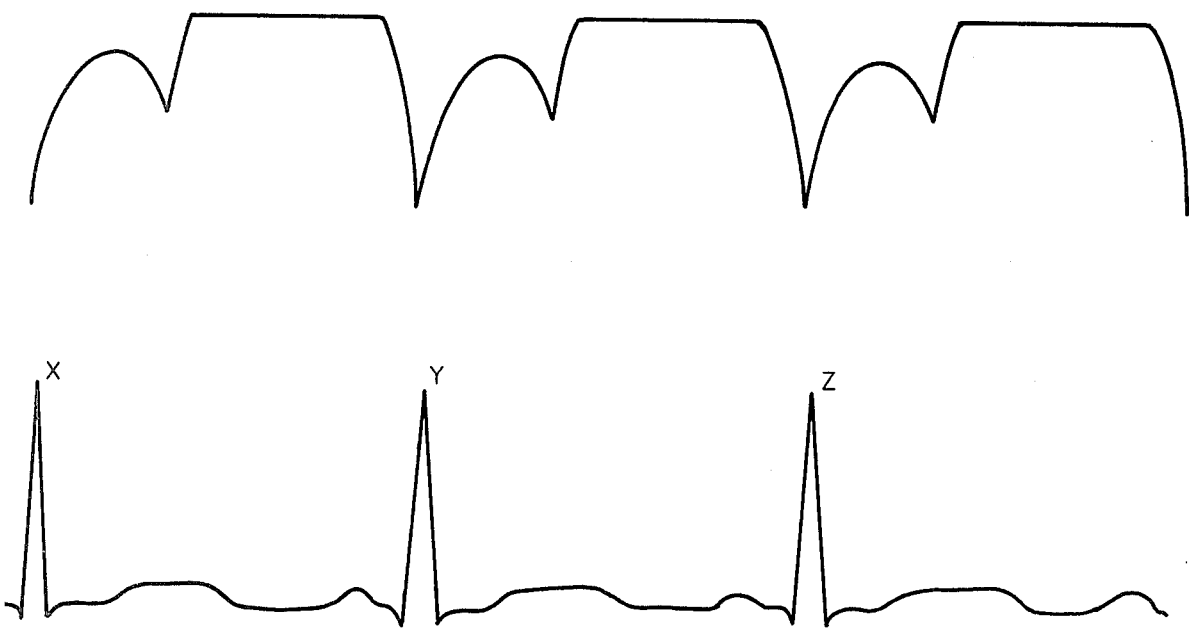
FIG. 9 is a timing diagram.
FIG. 10 is a trace of ECG and aortic pressure.

As described in the operation of the invention the waveform of the ECG is analyzed. The detection and analysis of this waveform per se is old and has not been described in detail. A clearer understanding of the relationship between the computer 16 and the control module 10 is illustrated in FIG. 10. In the automatic mode, assume that the heart cycles X and Y are past and that cycle Z is about to begin. If the timing adjustments for this cycle Z are required to be at the control module before the R-wave then the adjustments must be generated by the computer 16 during cycle Y. This implies that hemodynamic data collected during cycle Y cannot be used to generate these adjustments. A one cycle delay would then exist between data collection and implementation of timing adjustments based on that data. Since the assist device is always inactive during heart systole (the time when the ventricle ejects blood) then time during systole is used by the computer 16 to process data and transfer the timing adjustments. Instead of requiring that the adjustments for the cycle Z be at the control unit before the R-wave, the timing adjustments arrive before the systole ends. This allows the data collecting during the immediately preceding cycle, that is cycle Y, to be used to insure that adjustments arrive before the end of systole. The control module is designed to receive the data within the first 100 msec of heart systole, this is the "processing" period. If a fast heart rate of 3 beats per second is considered the period of the heart cycle is then 330 msec. Approximately one-third of this 110 msec would be heart systole. Thus the 100 msec processing time limit was selected. Obviously if this is inadequate it can be easily changed within the control unit.

Figure 11:
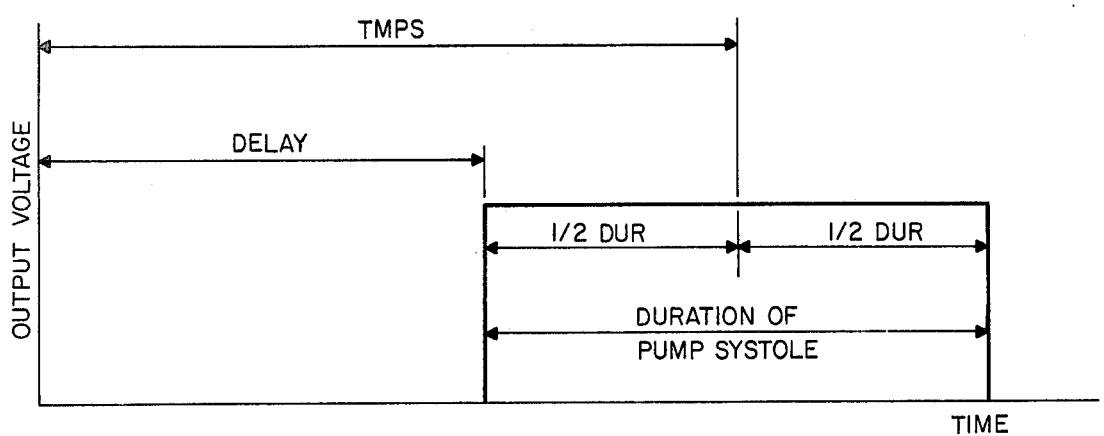
FIG. 11 is a comparison of the timing of prior art devices with our invention; and, FIG. 12 is a trace of ECG and a control pulse and aortic pressure.

The invention has been described in reference to the control module having replaced the conventional "delay" typically used with such assist devices. The TMPS alone controls the phase between the heart and pump cycles. A comparison of the inventive apparatus and conventional timing adjustments is shown in FIG. 11.

Figure 12:
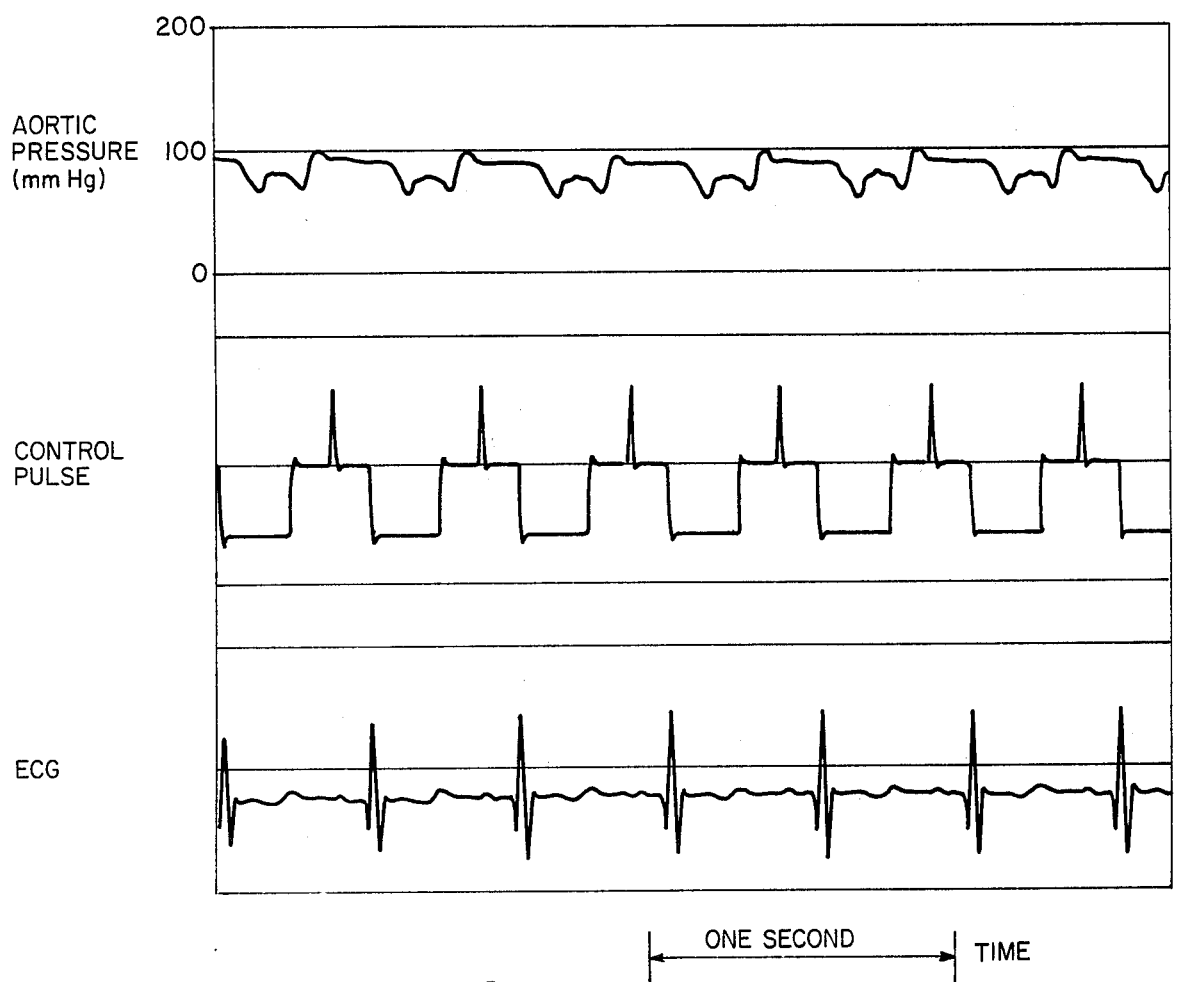

FIG. 12 illustrates results obtained when the inventive apparatus was used for intra-aortic balloon pumping in dogs. The bottom tracing shows the ECG signal used to synchronize the control module to the cardiac cycle. The center trace shows the output of the control unit. A reference pulse is superimpsoed over the control pulse to indicate TMPS. The leading edge of the reference pulse indicates the occurrence of the TMPS. The top tracing shows the resulting aortic root pressure. In the example shown here the period of the heart cycle was approximately 490 msec. TMPS was set to 350 msec and the "duration" was set to 26 msec.

As will be apparent to those skilled in the art, our invention may be used with any type of assist device, internal, external, etc.

Having described our invention, what we now claim is:

1. An apparatus to control a cardiac assist device which apparatus is responsive to an ECG signal and is adapted to activate and deactivate the assist device which comprises:
   (a) means to detect at least a portion of an ECG signal;
   (b) means to determine the time from the detected portion of the ECG signal to mid pump systole (TMPS) and the duration of the pump systole (DUR);
   (c) means to store the TMPS and the DUR, and to generate values based on the TMPS plus or minus one-half DUR, the means to store in communication with the means to determine; and, (d) a control module in communication with the means to detect and the means to store, the control module adapted to output signals to the assist device which signals control the time of activation and deactivation of the assist device, the signals output based on TMPS plus one-half DUR and TMPS less one-half DUR; the control module outputting these signals synchronous with the cardiac cycle as represented by the detected ECG signal.

2. The apparatus of claim 1 wherein the portion of the ECG signal which is detected is the R-wave.

3. The apparatus of claim 1 wherein the means to store includes means to analyze the ECG curve in a first cardiac cycle and to generate values of the TMPS and one-half DUR during said first cycle and to transfer said values to the control module for use during a second successive cardiac cycle.

4. The apparatus of claim 3 which includes means to disable the control module when a premature ventricular beat is sensed.

5. The apparatus of claim 3 wherein the control module includes a plurality of counters including a first start counter to activate the assist device and a second stop counter to deactivate the assist device.

6. The apparatus of claims 1 which includes means to disable the control module when a premature ventricular beat is sensed.

7. The apparatus of claims 1 wherein the control module includes a plurality of counters including a first start counter to activate the assist device and a second stop counter to deactivate the assist device.

8. A method of controlling a cardiac assist device which includes:
   detecting at least a portion of an ECG signal;
   determining the time from the signal detected to mid-pump systole (TMPS) and the duration of the pump systole (DUR);
   storing the TMPS and DUR;
   generating values based on the TMPS plus or minus $\frac{1}{2}$ DUR;
   controlling the time of activation of the device based on TMPS less one-half DUR and the time of deactivation of the device based on TMPS plus one-half DUR, by
   providing a signal to activate the assist device, and
   providing a signal to deactivate the assist device, these signals synchronous with the cardiac cycle as represented by the portion of the detected ECG signal.

9. The method of claim 8 wherein the detected portion of the ECG signal is the R-wave.

10. The method of claim 9 which includes:
    analyzing the ECG curve in a first cardiac cycle;
    generating values of the TMPS and the one-half DUR during said first cycle; and
    using the values of the TMPS and the one-half DUR generated during the first cycle during a second successive cardiac cycle to control activation and deactivation of the assist device.

11. The method of claim 8 which includes:
    disabling the assist device when a premature ventricular beat is sensed.

12. The method of claim 11 which includes:
    analyzing the ECG curve in a first cardiac cycle;
    generating values of the TMPS and the one-half DUR during said first cycle; and
    using the values of the TMPS and the one-half DUR generated during the first cycle during a second successive cardiac cycle to control activation and deactivation of the assist device.

13. The method of claims 8 which includes:
    analyzing the ECG curve in a first cardiac cycle;
    generating values of the TMPS and the one-half DUR during said first cycle; and
    using the values of the TMPS and the one-half DUR generated during the first cycle during a second successive cardiac cycle to control activation and deactivation of the assist device.

* * * * *